United States Patent
Vroom

(10) Patent No.: US 6,596,325 B1
(45) Date of Patent: Jul. 22, 2003

(54) COMPOSITION FOR THE TREATMENT OF HOOF CONDITIONS IN HOOFED ANIMALS

(76) Inventor: René Werenfridus Lodewijk Vroom, Meppelerweg 42, Ruinen (NL), 7963 RX ( * ) Notice: Subject to any disclaimer, the term of this patent is extended or adjusted under 35 U.S.C. 154(b) by 0 days.

(21) Appl. No.: 09/647,434
(22) PCT Filed: Apr. 1, 1999
(86) PCT No.: PCT/NL99/00243
§ 371 (c)(1),
(2), (4) Date: Jan. 23, 2001
(87) PCT Pub. No.: WO99/51089
PCT Pub. Date: Oct. 14, 1999

(30) Foreign Application Priority Data

Apr. 2, 1998 (NL) .............................. 1008795

(51) Int. Cl.[7] ................................. A61K 35/78
(52) U.S. Cl. ..................... 424/769; 424/725; 424/742; 424/746
(58) Field of Search ................. 424/725, 742, 424/746

(56) References Cited

U.S. PATENT DOCUMENTS

| | | | |
|---|---|---|---|
| 4,070,451 A | * | 1/1978 | Price |
| 4,530,828 A | * | 7/1985 | Smith et al. |
| 4,822,595 A | * | 4/1989 | Corliss et al. |
| 5,087,620 A | * | 2/1992 | Parab |
| 5,661,170 A | * | 8/1997 | Chodosh |
| 5,760,052 A | * | 6/1998 | Peacock |
| 5,840,283 A | * | 11/1998 | Sorenson et al. |
| 5,889,039 A | * | 3/1999 | Knowles |
| 5,985,934 A | * | 11/1999 | Gaffney et al. |

FOREIGN PATENT DOCUMENTS

| | | | |
|---|---|---|---|
| DE | 33 16 599 A1 | | 5/1983 |
| GB | 1996-162167 | * | 4/1996 |
| GB | 1997-453944 | * | 8/1997 |
| JP | 404244026 A | * | 9/1992 |
| SU | 1741724 A1 | * | 6/1992 |
| WO | WO 88/06884 | * | 9/1988 |
| WO | 89/07385 | | 8/1989 |

OTHER PUBLICATIONS

Regos et al., "Antimicrobial spectrum of triclosan, a broad spectrum antimicrobial agent for topical application", Dermatologica, 1979, 158(1):72–9, abstract.*
The Merck Index, 10th edition, 1983.*
"Bay leaf", Chemoffice 2001, Home Care 2 (p.8/10).*
Budavari, Susan, et al. *The Merck Index, An Encyclopedia of Chemicals, Drugs and Biologicals.* Twelfth Edition, 1996, pp. 717–718; p. 1551; p. Ther–5–Ther10; p. Ther–15–16.

* cited by examiner

Primary Examiner—Leon B. Lankford, Jr.
Assistant Examiner—Ruth A. Davis
(74) Attorney, Agent, or Firm—Hoffmann & Baron, LLP

(57) ABSTRACT

Composition for the topical treatment of hooves of hoofed animals comprising a curing agent preferably comprising bay leaf oil and/or turpentine oil and a fungicide, and optionally a bactericide. A method for the preparation of the composition. A method of treatment of hooves of hoofed animals suffering from white line disease, hoof thrush and/or hoof rot. Use of a fungicide and optionally a bactericide in the manufacture of a composition for topical treatment of diseased hooves of hoofed animals.

2 Claims, 1 Drawing Sheet

Figure 1:
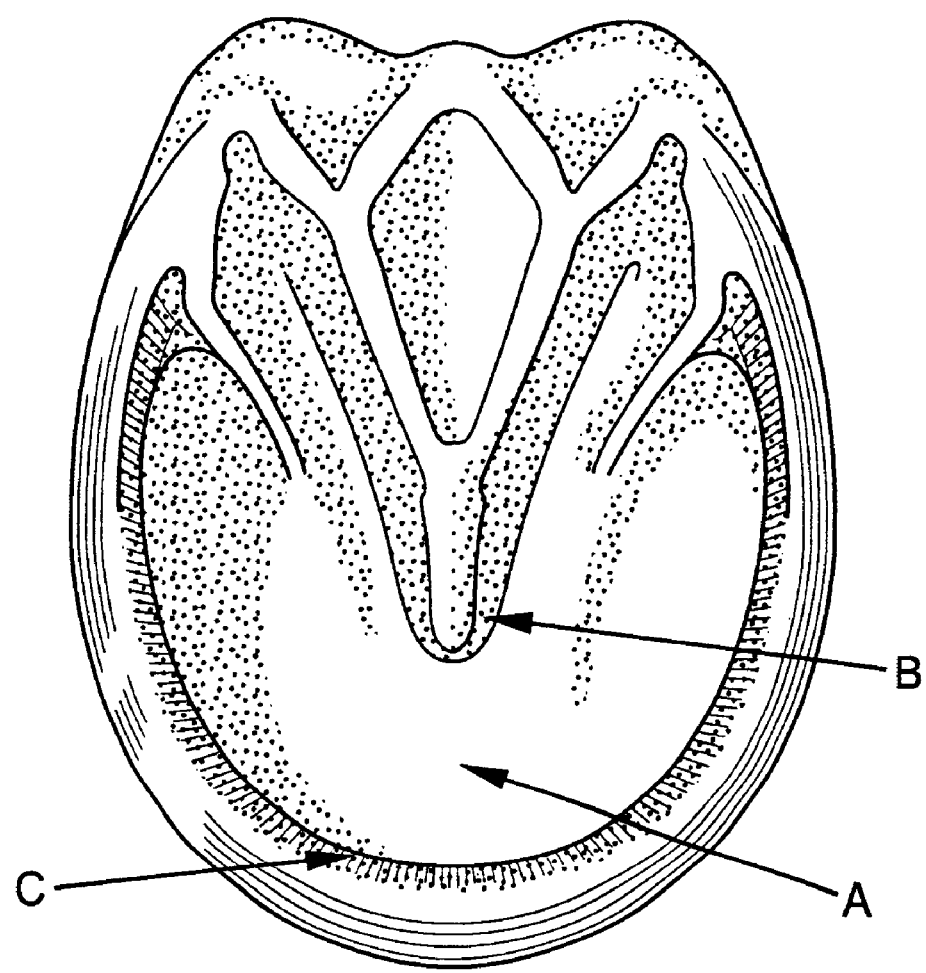

A: Hoofsole
B: Thrush
C: White line

COMPOSITION FOR THE TREATMENT OF HOOF CONDITIONS IN HOOFED ANIMALS

The present invention relates to a composition for the treatment of hooves in (one- and/or two-) hoofed animals and a method for the treatment of hoofed animals.

The invention is also directed to a new and improved method for treating white line disease and hoof thrush in horses or in other equine animals susceptible to hoof thrush and white line disease and for treating hoof rot in sheep, goat and cattle. By "equine animals" is meant a horse, donkey, mule, burro or zebra. However, the preferred animal is a horse. Hereinafter, the term "horse" encompasses all equine animals.

White line disease in horses is a disease that has not been very well documented. White line disease can cause severe discomfort for the horse and, if not well groomed, the horse will become cripple or lame.

The white line is generally considered to be that section of the hoof where the farrier places the nails when shoeing the horse. The white line disease is an affection of the stratum internum, which is the inside part of the hoof. The disease will cause a disruption of the white line, other than the disruption caused by normal influences from the outside such as small stones, sand and the like. The disruptions caused by such normal influences are usually superficial and will disappear upon regular trimming of the hoof. The white line disease generally tends to spread out more and deeper into the hoof. If the disease spreads out at proximal distance a void will form. The void will be surrounded by the horn of the stratum lamellatum on one side and the stratum internum or medium on the other side. This situation is commonly known as "hollow wall". The hoof then becomes brittle. The horse will experience considerable discomfort from this situation. The generally used remedy to limit the damage is regular and extensive trimming of the hooves. However, in many cases this does not solve the problem of white line disease.

By hoof thrush is meant a disease in horses of the hoof and frog tissue caused by a variety of pathogenic micro-organisms. By hoof rot is meant an analogous disease of the hoof in sheep, goats and cattle. The diagnostic signs of thrush disease or hoof rot include a strong unpleasant odour and discharge from the frog tissue. A veterinarian of ordinary skill can readily determine whether a horse exhibits a thrush infection or white line disease or whether a sheep, goat or cow exhibits a hoof rot infection.

A schematic drawing of the hoof is given in FIG. 1.

In an article in the "Tijdschrift voor Diergeneeskunde, 1995, 120, 18, pp 526–529", white line disease has been investigated in a population of horses in the Netherlands. A mycological investigation of the hoof material was carried out. It was found that *Scopulariopsis brevicaulis* was detected in 60% of the animals with an abnormal white line or with hollow wall or with seedy toe. The reported remedy against white line disease, hollow wall or seedy toe is based on the conventional treatment which is the extensive trimming of the hooves and removal of affected material. Other remedies or treatments are not given or suggested.

From WO89/07385 it is known that hoof thrush in horses and hoof rot in other animals is primarily caused by an anaerobic bacterium, *Spherophorus necrophorus*. The application describes a remedy based on the use of metronidazole (1-(2-hydroxyethyl)-2-methyl-5-nitroimidazole) in various forms and treatments.

It has now been found that a composition comprising a curing agent and a fungicide is very effective in the treatment of white line disease, hoof thrush and hoof rot. The invention thus relates to a composition for the topical treatment of hooves of one- and/or two-hoofed animals comprising a curing agent and a fungicide.

The curing agent in the composition is in general an agent which has a antiseptic and/or disinfecting effect. The curing agent, or caring agent, can also have other characteristics which can attribute to the well being of hooves. The active components in the curing agent are selected from the group consisting of bay leaf oil, medicinal turpentine oil, tea tree oil, lavender oil, bergamot oil, eucalyptus oil, pine oil, rosemary oil or mixtures and combinations thereof, preferably bay leaf oil, medicinal turpentine oil and/or tea tree oil or mixtures and combinations thereof. The curing agent is present in an amount up to 30 wt. %, preferably from 5 to 25 wt. %, more preferably from 10 to 20 wt. %. The fungicide in the composition can be any suitable fungicide as long as it is active against the fungus that is found in white line disease, hoof thrush or hoof rot. Preferably the fungicide expresses activity towards *Scopulariopsis brevicaulis*. The fungicide is selected preferably from the group consisting of enilconazole, clotrimazole, miconazole, sulconazole, econazole, oxiconazole, tioconazole, thiabendazole, naftifine, terbinafine, tolnaftate, itraconazole or mixtures and combinations thereof, preferably enilconazole, clotrimazole, miconazole or mixtures and combinations thereof. The fungicide is present in an amount up to 20 wt. %, preferably from 5 to 15 wt. %, more preferably from 7 to 12 wt. %. In a preferred embodiment the invention encompasses a composition for the topical treatment of hooves comprising

|  |  | preferably |
|---|---|---|
| Curing agent | up to 30 wt. % | 5–25 wt. % |
| Fungicide | up to 20 wt. % | 5–15 wt. % |
| Emulgator | up to 50 wt. % | 20–30 wt. % |
| solvent/diluent | to 100 wt. % | to 100 wt. % |

In different embodiments, such as an ointment, the composition may additionally comprise compounds such as a cetylester or like compounds. For use as a conditioner a basis composition can be prepared which can subsequently be diluted to a concentration that is suitable for application to the hoof. Alternatively the composition can be in the form of a gel. The previously described afflictions of hooves are also influenced by the presence of bacteria. If the hoof suffers from these afflictions, bacteria may enter the damaged areas and cause further infections. This will not only cause additional discomfort, but also have a detrimental influence on the healing process in general. To avoid this, it is possible and desirable to have a bactericide present in the composition according to the invention. The bactericide is preferably selected from the group consisting of chloroxylenols, triclosan, chlorhexidine, octopyrox or mixtures and combinations thereof, preferably triclosan and/or chloroxylenols or mixtures and combinations thereof. The fungicide is present in an amount up to 20 wt. %, preferably from 5 to 15 wt. %, more preferably from 7 to 12 wt. %. The composition can be provided in any suitable form such as a solution, emulsion, powder, ointment, spray, gel etcetera. The composition can be further brought in a suitable form by the addition of diluents, carriers, excipients, adjuvants, emulgators, dyes, colorants, perfumes and the like. The composition can also be mixed with known products for grooming or tending of hooves.

The present invention also relates to a method for treating white line disease, hoof thrush (in a horse) or hoof rot (in a sheep, goat or cow) comprising topically administering a therapeutically effective amount of the composition in a carrier directly on a thrush or hoof rot infected area for a treatment period effective to cure the thrush or hoof rot infection.

The present invention encompasses a method for the topical administration of the composition in the form of a solution or in the form of a gel, salve or ointment at and/or near the area affected by white line disease or the thrush or hoof rot infected area.

For topical administration in the form of a solution, the active drug component of the present invention, in liquid, powdered or lyophilised form may be combined with a suitable pharmaceutical diluent or carrier (collectively referred to herein as "carrier" materials) such as water, saline, aqueous buffers, and the like. The method of application of the composition in the form of a solution may be by pouring, squirting, flushing or sponging the solution on the thrush or hoof rot infected area. In a preferred embodiment for treating thrush, a disposable plastic syringe (without a needle) may be filled with some of the composition solution for treatment and squirted on the thrush infected is area. Alternatively, the horse's hoof may be submerged or immersed or soaked in the solution according to the invention to effect the treatment. In severe cases, such a soaking treatment may be necessary to effectively cure the thrush. In a preferred embodiment for treating hoof rot, the sheep, goat or cow is walked through a foot bath containing the solution.

The hooves of the animals in general are also carriers of bacteria and may even be infected by bacteria, for example by dung or faeces. When the same solution is used to treat different animals cross-contamination of the hooves between the animals may occur. The presence of the bactericide in the composition can also account for the prevention of cross-contamination.

For topical administration in the form of a gel, salve or ointment, the composition as above may be combined with a suitable carrier. The method of application of the composition in the form of a gel, salve or ointment may be by contacting and rubbing the gel, salve or ointment on, in, around and throughout the thrush hoof rot or white line disease infected areas of the animal's hoof and frog.

Regardless of the form and method of administration selected (e.g. solution, gel, salve, ointment), the composition is formulated into pharmaceutically acceptable dosage forms by conventional methods known to those skilled in the art.

Regardless of the form and method of administration selected, a non-toxic but therapeutically effective amount of the composition is employed in any treatment. The dosage regimen for treating white line disease, hoof thrush or hoof rot is selected in accordance with a variety of factors, including the medical condition of the animal, the severity of the infection and the form of administration. A veterinarian of ordinary skill can readily determine and prescribe the effective amount required to cure the infection. In so proceeding, the veterinarian could employ relatively low doses at first and subsequently increase the dose until a maximum response is obtained.

With the composition according to the invention the treatment of hooves can effectively be achieved by treating horses over a period of, for instance, twelve to twenty weeks by a footbath three times a week during five or ten minutes. After that it is advantageously to apply a weekly footbath as a preventive treatment. An advantage of the invention is that the horn of the hooves improves in quality and the growth of horn is stimulated.

A composition according to the invention, wherein the active components are incorporated in an emulsion in water, is one wherein the composition comprises 5–10% bay leaf oil, 0.1–0.2% medicinal turpentine oil, 20–30% cetylester such as cetyl palmitate and/or cetylstearate, 5–8% miconazole or enilconazole or itraconazole, 20–30% of an emulgator such as a polysorbate and or a laurate, preferably sorbitollaurate in an organic solvent such as ethanol or methanol, the composition is diluted with about 50 parts of an aqueous solution.

A most preferred composition is one wherein the composition comprises 9% bay leaf oil, 0.15% medicinal turpentine oil, 23% cetylester such as cetyl palmitate or cetylstearate, 6.6% miconazole or enilconazole, or itraconazole, 25% of an emulgator such as a polysorbate and/or a laurate, preferably sorbitollaurate in an organic solvent such as ethanol or methanol, the composition is diluted with about 50 parts of an aqueous solution.

The invention also encompasses a method for the preparation of the composition according to the invention.

A preferred example of the method according to the invention comprises the steps of:

a. homogenising bay leaf oil, medicinal turpentine oil and cetylester;

b. homogenising miconazole or enilconazole or itraconazole with emulgator and solvent until a homogenous solution or suspension is obtained;

c. mixing and homogenising the mixtures obtained in the previous steps.

To obtain a composition which can be readily used, the following additional steps are performed:

d. mixing and homogenising a part of the composition obtained under c with an equal part of water with a temperature of 60–80° C.;

e. adding, mixing and homogenising another two parts of water with a temperature of 60–80° C.

It is to be noted other sources of ingredients or other ingredients than the above described can be used. For instance, by starting from the pure and commercially available compounds, the process for the preparation of the composition may deviate from the one herein described in a manner which is obvious to the man skilled in the art, without detracting from the gist of the invention. It is also possible to employ commercial available compositions comprising curing agents, fungicides and bactericides, respectively. The different compositions are mixed until a suitable homogenous composition is obtained by using variations of the process which variations are known to the man skilled in the art.

The obtained emulsion is diluted with 50 parts water and homogenised. A footbath is filled with this solution until a depth of about 5 cm. The horses are placed in the solution for a period of 5–10 minutes. It is advantageously to treat all horses, not only the horses with the afflictions as mentioned and to continue the treatment until all horses are free from the afflictions. After that it is advisory to continue the treatment on a more or less regular basis for instance every two weeks.

By not diluting the mixture obtained under e. an ointment is obtained which can be used as such.

The ointment can advantageously be used for the prevention of the mentioned afflictions by applying the ointment previously to the shooing of the horse.

The mixture and the solution prepared from the mixture can advantageously be used with sheep, goat and cow when hoof related infections or hoof rot occur.

EXAMPLES

Composition

An aqueous solution of 100 liter was prepared with the following ingredients:
- 2020 ml of a concentrated solution of enilconazole, containing 100 mg/ml enilconazole (obtained from Janssen-Cilag, brandname Imaverol)
- 3 liter of a solution containing chloroxylenol (4-chloro-3,5-dimethylphenol, obtained from Sigma-Aldrich) in 96% ethanol
- 1250 ml of a composition containing 280 mg/g bay leaf oil and 1.5 mg/g turpentine oil.

Some preferred compositions that can be used for different treatments of hooves are summarised in the following table, all amounts are grams per 1000 gram of the total composition.

|  | cleaner | conditioner | ointment | anti thrush |
|---|---|---|---|---|
| curing agent | 1 | 10 | 270 | 5 |
| fungicide | 1 | 28 | 11 | 20 |
| bactericide | 1 | 15 | 11 | 20 |
| cetyl ester or other basis | >0 | >0 | 708 | >0 |
| emulgator | + | 20 | >0 | >0 |
| solvent |  | 120 (ethanol) |  |  |
| Balance | conventional shampoo | water |  | ethanol/ water |
| sequestrans /detergent | + |  |  |  |

+ = present in unknown amount

The different compositions can be used as follows:

Hoof cleaner can be used as a regular shampoo.

The conditioner is in the form of an emulsion which can be diluted 10–20 fold, preferably 14 fold. The conditioner can be applied as a solution for instance in a bucket or a hoof bath.

The ointment can be used as such. The anti thrush composition is in the from of a thin viscous gel which is used as such and can be applied with a tampon.

The table contains the preferred compositions of the different embodiments. The curing agent, the bactericide and the fungicide may be combinations of the respective curing agents, bactericides and fungicides. For instance, in the compositions of the table the curing agent is a mixture of bay leaf oil, medicinal turpentine oil and tea tree oil 2/2/1 w/w/w, the fungicide is enilconazole/clotrimazole/miconazole 1/1/1 w/w/w, and the bactericide is chloroxylenol/triclosan 1/1 w/w.

1. Flushing

In general, each hoof to be treated was cleaned with a hoof pick. The pick was used to remove material in and around the frog and heel. In some cases, the hooves were not preliminarily cleaned with a hoof pick, but treated directly with the solution containing the composition.

The solution can be applied by spraying or with a syringe.

2. Soaking

Several horses were treated by soaking the hooves in the solution. In general, a bath or a bucket was filled with the solution. Each thrush infected hoof, after it was cleaned with a hoof pick, was placed in the bucket containing the solution and was completely submerged and soaked in the solution for approximately 20 minutes. Each hoof was submerged and immersed in the solution. The time of soaking ranged from approximately 20 seconds to 60 minutes.

Soaking of the hooves can be accomplished in a variety of manners which will be sketched below;

1. Each hoof is placed separately in a bucket. The bucket contains the solution. The hoof is submerged and soaked during a period of approximately 20 minutes.

2. The horse is lead into a treatment box. The box restrains the movement of the horse and the bottom of the box is a bath. After the horse is placed in the box, the bath is filled with the solution containing the active components. The hooves are completely submerged and soaked in the bath to allow the active ingredient to reach all clefts and crevices of the hoof. The bath can also contain a spongy mat which is soaked with the solution.

3. The horse is being treated with a rinsing shoe. The leg of the horse is placed in the rinsing shoe and the rinsing shoe is then filled with the solution. The hoof is soaked in the solution.

4. The horse is being treated with an easy boot, generally used for damaged hooves. The shoe is applied and filled with the solution and the hoof is soaked.

5. The horse is being treated with an easy boot, whereby the boot is filled with cotton balls soaked in the solution.

6. The voids in the hoof are filled with cotton balls which are soaked in the solution and subsequently wrapped in (self-adhesive) bandages.

7. A horseshoe whereby between the iron and the hoof a plate of plastic or leather is applied. The hoof is filled with cotton balls soaked in the solution. The plate will keep the cotton balls in place. This can also be accomplished with an iron plate which is attached to the horseshoe with bolts or clamps.

8. A textile bag lined with leather or plastic is placed around the hoof and filled with the solution containing the active ingredient.

The above described methods of treatment are intended to be exemplary only, other methods of treatment are imminent to the skilled practitioner. The essence is that by soaking the hooves an effective treatment of the hooves with the active ingredient is obtained and the active ingredient is allowed to reach all clefts and crevices of the hoof.

Example 2

Treatment of Thrush Infected Hooves Using Ointment

Treatment Procedure

Preliminarily, each hoof to be treated was cleaned with a hoof pick as previously. The pick-cleaned hoof was lifted and held while the ointment containing the active ingredients of the composition was rubbed on, in, around and throughout the affected white line and the voids or the thrush infected areas of the hoof and frog tissue, including the sulcae of the frog tissue. The ointment was sometimes applied using a brush to insure that the ointment gets into all clefts and crevices of the heel and frog tissue. The treated hoof may be left exposed or may be covered with paper to protect the treated hoof. A paper covering of the hoof was prepared as follows. The shape of the hoof was traced onto a brown paper bag. The paper was then cut to the shape of the hoof and shoe. The paper was trimmed to fit inside the hoof and was tucked under the shoe, where it remained as a protective cover for the treated hoof.

Another way of treating the frog tissue is to use a cotton ball immersed in a concentrated solution of the composition according to the invention. The cotton ball is placed in the groove which is caused by the thrush. The cotton ball is refreshed on a regular basis.

The grooming of the hoof is necessary. During the washing or bathing the natural protection from the hoof will be removed. Therefore it is advisable to apply an ointment on the hoof after bathing.

It is most preferred that after soaking in anyway of the hoof with the solution the hooves are treated with an ointment containing the composition according to the present invention.

Example 3

Treatment of Hoof Rot Infected Hooves

Preparation of the Foot Bath

The solution is poured into a foot bath to yield a solution in the foot bath that is 5–7 cm deep so as to allow immersion of the animal's hoof up to the coronet band or hairline. The dimensions of the foot bath should be such that it takes 15–30 seconds for the animal to walk through the foot bath.

Treatment Procedure

Preliminarily, each hoof to be treated may be (but need not be) cleaned with a hoof pick to remove packed material in and around the frog and heel. Each sheep, goat or cow to be treated is then walked through a foot bath prepared. The period of each treatment should be at least 15–30 seconds.

Treatments of Different Horses

Several horses have been treated, using procedures as described previously. The results are summarised below;

Horse 1 (by the name of Kigali): The horse suffered from hoof thrush on all four hooves. The horse has been treated with the anti-hoof thrush formulation for the period of one week. Every day a fresh cotton ball was placed in the thrush, one day with the formulation, the other day a clean cotton ball was applied. Result: After a week the affected thrushes dried. After two weeks the thrushes had a healthy look and showed a normal development.

Horse 2 (Jerremy): The horse suffered from a combination of hoof thrush and white line disease. Treatment was carried out in the hoof bath and in a similar manner to horse 1. After two weeks the hoof thrush was cured. The white line disease was treated over a period of five months during which twice a week the horse was placed in the hoof bath and after bathing the hooves were treated with the ointment. After this treatment the hooves were trimmed and returned to the normal model and quality. The structure of the hoof was tougher and therefore the hoof was stronger.

Horse 3 (Ideaal): All four hooves were strongly inflicted by white line disease. During six months the horse was treated in a hoof bath. During the treatment the quality of the hooves markedly improved.

Horse 4 (Voltaire): The horse had two different hooves, one normal, the other flat and weak. By treating the bad hoof in the hoof bath, the hoof obtained a better structure and the form returned to normal.

Horse 5 (Ike): The horse suffered from a light form of white line disease. During two months the horse was treated twice a week in a hoof bath and a third month the treatment was reduced to once a week. After bathing and in between treatment the hooves were treated with the ointment. The result was that the hooves were free of afflictions.

Horse 6 (Fjord): The horse had two affected hooves. After treatment during three months, the hooves were again in a good condition.

What is claimed is:

1. A method of treatment of hooves of hoofed animals comprising contacting the hooves with a composition comprising a curing agent and a fungicide;

wherein the fungicide is selected from the group consisting of enilconazole, clotrimazole, miconazole, sulconazole, econazole, oxiconazole, tioconozole, thiabendazole, naftifine, terbinafine, tolnaftate, itraconazole and mixtures or combinations thereof;

wherein the curing agent is selected from the group consisting of bay leaf oil, medicinal turpentine oil, tea tree oil, lavender oil, bergamot oil, eucalyptus oil, pine oil, rosemary oil and mixtures or combinations thereof; and wherein the hoofed animal suffers from white line disease, hoof thrush or hoof rot or combinations thereof.

2. A method of treatment of hooves of hoofed animals comprising contacting the hooves with a composition comprising a curing agent, a fungicide and a bactericide;

wherein the fungicide is selected from the group consisting of enilconazole, clotrimazole, miconazole, sulconazole, econazole, oxiconazole, tioconozole, thiabendazole, naftifine, terbinafine, tolnaftate, itraconazole and mixtures or combinations thereof;

wherein the curing agent is selected from the group consisting of bay leaf oil, medicinal turpentine oil, tea tree oil, lavender oil, bergamot oil, eucalyptus oil, pine oil, rosemary oil and mixtures or combinations thereof, and wherein the hoofed animal suffers from white line disease, hoof thrush or hoof rot or combinations thereof.

* * * * *

UNITED STATES PATENT AND TRADEMARK OFFICE
CERTIFICATE OF CORRECTION

PATENT NO.     : 6,596,325 B1
DATED          : July 22, 2003
INVENTOR(S)    : René Vroom It is certified that error appears in the above-identified patent and that said Letters Patent is hereby corrected as shown below:

Column 3,
Line 22, now reads "infected is area" should read -- infected area --

Column 5,
Line 43, now reads "is in the from" should read -- is in the form --

Signed and Sealed this

Ninth Day of September, 2003

JAMES E. ROGAN
*Director of the United States Patent and Trademark Office*